United States Patent [19]

Mobin-Uddin

[11] Patent Number: 4,651,733

[45] Date of Patent: Mar. 24, 1987

[54] BLOOD VESSEL HOLDING DEVICE AND SURGICAL METHOD USING SAME

[76] Inventor: Kazi Mobin-Uddin, Suite 115, 393 E. Town St., Columbus, Ohio 43215

[21] Appl. No.: 767,890

[22] Filed: Aug. 21, 1985

Related U.S. Application Data

[63] Continuation-in-part of Ser. No. 617,943, Jun. 6, 1984, abandoned.

[51] Int. Cl.[4] ............................................. A61B 17/00
[52] U.S. Cl. ................................. 128/303 R; 128/20
[58] Field of Search ...................... 128/20, 329 R, 314, 128/303 R

[56] References Cited

U.S. PATENT DOCUMENTS

| | | | |
|---|---|---|---|
| 1,006,052 | 10/1911 | Boffin | 128/303 R |
| 1,708,578 | 4/1929 | Hyde | 128/20 |
| 3,467,079 | 9/1969 | James | 128/20 |
| 3,533,411 | 10/1970 | McKnight et al. | 128/329 |
| 3,687,139 | 8/1972 | Poirier | 128/329 |
| 3,749,099 | 7/1973 | Cotley | 128/329 |
| 3,857,386 | 12/1974 | Ashbell | 128/20 |
| 3,938,499 | 2/1976 | Bucalo | 128/334 |
| 4,372,302 | 2/1983 | Akerlund | 128/303 R |
| 4,462,401 | 7/1984 | Burgio | 128/303 R |

FOREIGN PATENT DOCUMENTS 2730164  8/1978  Fed. Rep. of Germany ........ 128/20

OTHER PUBLICATIONS

The Surgical Armamentarium, American U. Mueller ©1980, pp. 694–695.

Primary Examiner—Paul J. Hirsch
Attorney, Agent, or Firm—Buell, Ziesenheim, Beck & Alstadt

[57] ABSTRACT

A surgical blood vessel holding device is described having shank means in a middle region with a holder on one end and a narrow prong on the other end. The prong is provided with a hook extending laterally from the side thereof. The prong is adapted to be inserted into the open end of a blood vessel until the hook reaches the distal end of the vessel. The hook then pierces the vessel wall, allowing the device to dispose the end of blood vessel in facing relationship with respect to an opening in the wall of another blood vessel. The blood vessel can be locked onto the hook. Thereupon, suturing of the vessels is initiated, but not completed. The prong is then unhooked and removed and the suturing process is completed without the device to provide a continuous blood flow path between the two blood vessels.

30 Claims, 11 Drawing Figures

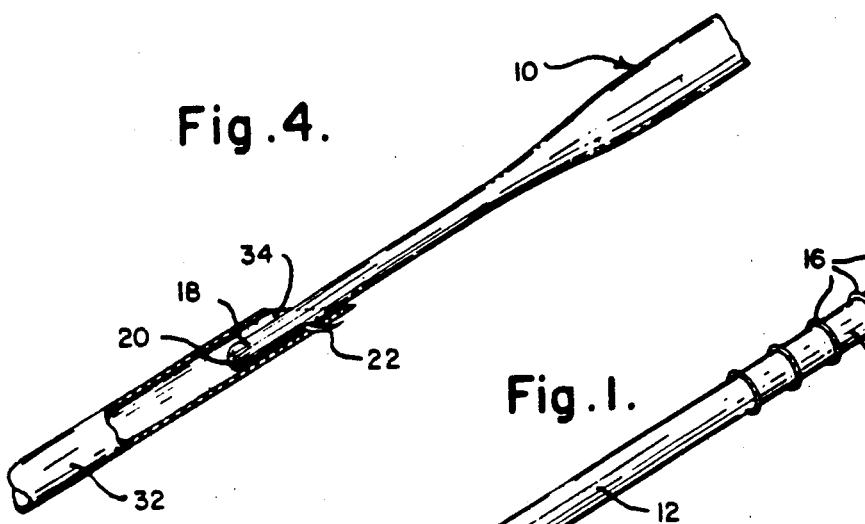
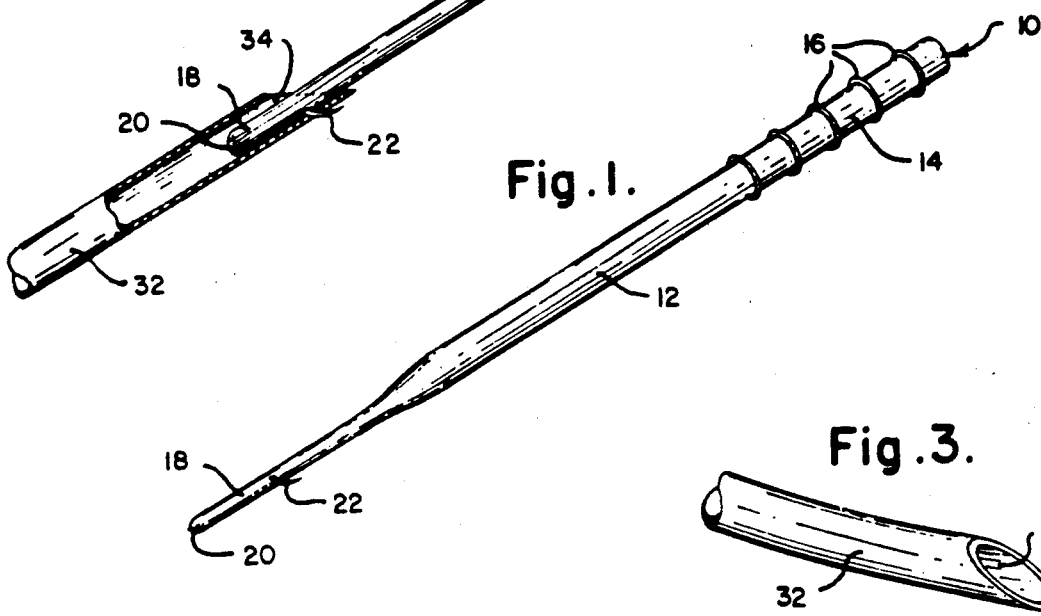
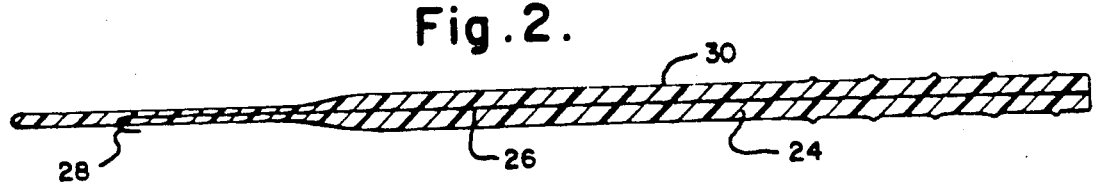
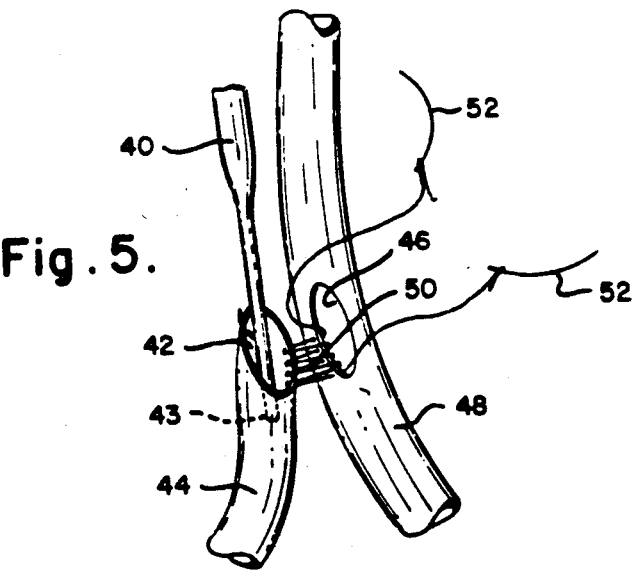

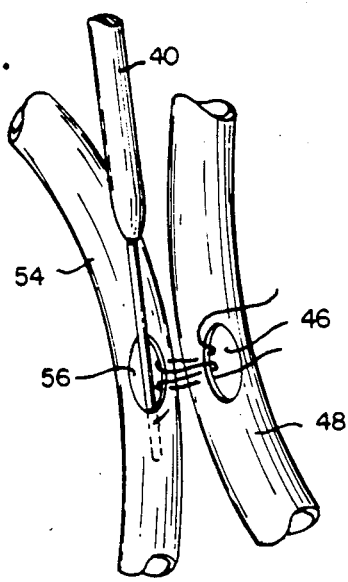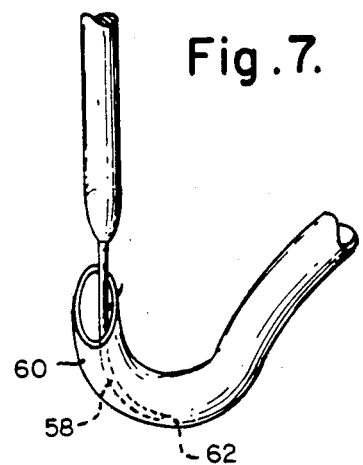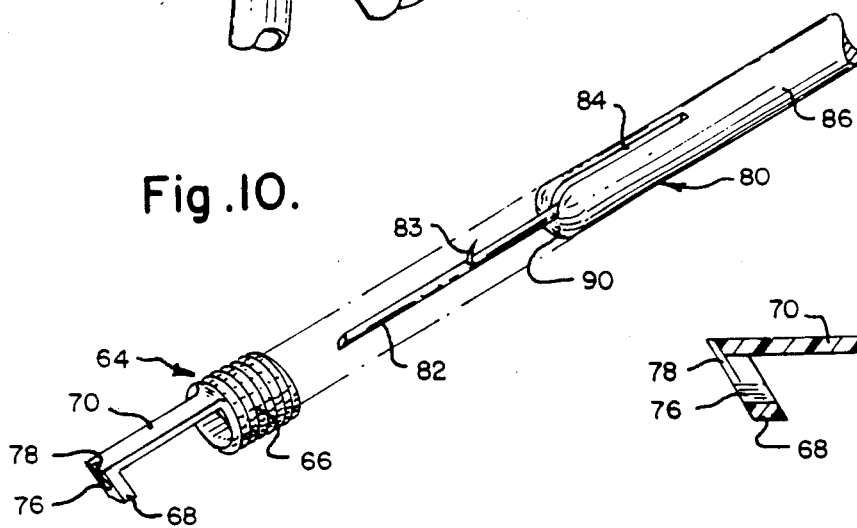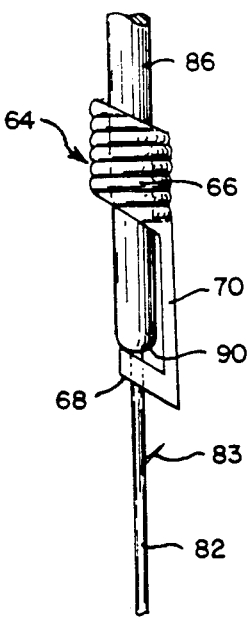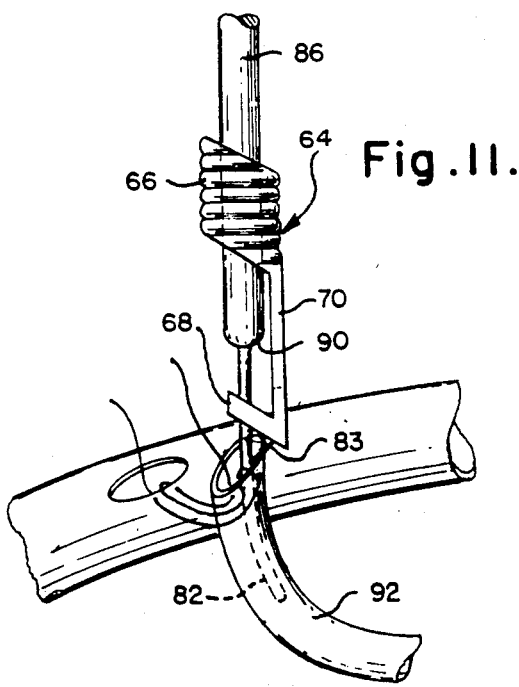

BLOOD VESSEL HOLDING DEVICE AND SURGICAL METHOD USING SAME

This application is a Continuation-In-Part of my application Ser. No. 617,943, filed June 6, 1984 now abandoned.

This invention relates to a surgical blood vessel holding device and to a method of anastomosis using this device.

The blood vessel holding device is particularly adapted for holding an open-ended vein in a desired position while attaching the open end of the vein to a side opening on another blood vessel, such as the aorta or any of its branches. The blood vessel holding device is also adapted for side to side anastomosis. The present invention is particularly adapted for use during coronary bypass and peripheral vascular surgery. It is adaptable for holding not only a vein, but also any synthetic grafts used as a blood vessel, like Dacron or Gortex grafts.

During vein bypass graft surgery, forceps are commonly used to hold and suspend the slanted or beveled open end (fish mouth opening) of a vein in close proximity to the opening on the wall of the aorta while sutures are being taken. The forceps can easily slip from its position during the anastomosis. Moreover, the inner wall of the vein is very susceptible to damage due to the holding or stretching of the vein by the forceps. These problems are obviated by the device of the present invention.

The surgical device of this invention is elongated and simulates a slender rod adapted to provide five regions including a handle region on one end; a middle or shank region; a prong or finger on the other end; a rounded nose at the terminus of said finger; and a sharply pointed hook extending laterally, preferably in a rearwardly direction, from an intermediate point on said finger.

The handle region can be shaped as a handle or it can have ridges or other means for frictional grasping and for physical identification of the handle end of the device.

The shank is located in the middle region of the device. It is intended to give length to the instrument to permit the reaching of difficult-to-reach areas. The shank can be rigid or it can be constructed of a flexible material to permit its bending into various shapes as required during use. After bending into any particular shape, it can be straightened back into its original shape.

The finger or prong of the device is at the end of the shank opposite from the handle or holder. It is adapted to be inserted into the open end of a blood vessel, particularly into the fish mouth opening of a vein or graft. It is also adapted to extend laterally across the end opening of a vein to serve as a brace for preventing closure of the end opening during an anastomosis procedure. The finger or prong can be constructed of a flexible material to enable it to adjust to the curvature of the vein or graft during anastomosis. The flexible prong can be employed where a rigid prong would tend to injure an opposite vein wall.

The nose constitutes the terminus of the prong. It is preferably smooth and rounded to facilitate insertion of the prong into the open end of a vein or to exert a bracing force against the inner wall of a vein near the open end thereof to maintain the end open during an anastomosis procedure.

The hook can be a sharply pointed needle or wire protruding laterally from the side of the finger. It is adapted for penetration of the wall of a vein or graft preferably at or near the apex of the fish mouth opening. The hook can conveniently protrude both outwardly and rearwardly, or primarily rearwardly, with respect to the nose. A convenient location for the hook is about 21 millimeters up from the nose, but other positions from the nose will also be useful. During use, the vein is slid up the finger of the device until substantially the most distal edge of the fish mouth shape can be snagged by the hook.

If desired, the device can be provided with a locking clip which is slidably mounted around the device. When the sliding clip is in the back position, it reveals the protruding needle. In the forward position, the sliding clip locks the protruding needle onto the vein or graft.

In a surgical method using the device of this invention, the distal end of the vein holder, i.e. the nose and the finger, is inserted into the interior of a vein through a fish mouth opening. The vein is slid up the finger until the most distal edge of the fish mouth shape can be caught by the protruding needle. Thereupon, the needle pierces the wall of the vein. Thereby, the device both braces and secures the vein. By proper positioning of the device, the opening of the vein is suspended adjacent to an opening made in the wall of an artery.

At times, the vein, once hooked in position, can slip off the hook if tension being applied is slightly eased up. The amount of tension being applied is a judgment and coordination type of function. To help reduce the tediousness of use and the possibility of the vein slipping off the hook, a locking clip can be mounted on the vein holder. The locking clip is longitudinally slidable and when in the back position exposes the hook point. When the clip is slid forward, it traps the lip of the vein onto the hook. The clip must then be slid back to effect the release of the vein. The clip also serves as a protecting cover for the point during handling and shipping.

If desired, the distal end of the vein holder can be disposed laterally across the fish mouth opening of the vein so that the needle pierces the wall of the vein from the inside at or near the apex of the fish mouth opening and the nose presses against the inside wall of the vein near the base of the fish mouth opening to prevent collapse of the opening during an anastomosis procedure.

At least a single suture is taken between the artery and the fish mouth opening of the vein while the vein is being secured by the vein holder. The suture can be repeated a number of times to provide a continuous, but loose, suture which is not pulled tight. After sufficient stitches are taken to support the vein, the holding device is unhooked and the prong is removed from the vein. Thereupon, the two edges of the suture are pulled more tightly, additional sutures are taken and the anastomosis procedure is completed.

It is seen that the blood vessel holding device holds the fish mouth opening of the vein securely in the desired position at the outset of the anastomosis. The finger portion of the device which is inserted into the vein acts as a splint and prevents collapse of vein edges. It also acts as a rigid deflector for the needle inside the vein as each suture is taken.

During the suturing, the edges of the fish mouth opening of the vein are suspended initially by the holding device and then gradually by the sutures taken between the edges of the vein opening and the artery opening. The device thereby allows for better visibility and simplified suturing techniques. Thereby, the blood vessel holding device allows the surgeon to make the anastomosis with great precision and in less time.

These and other advantages of the invention will become apparent by reference to the accompanying figures in which FIG. 1 is an isometric view of a metallic blood vessel holding device of this invention;

FIG. 2 is a longitudinal cross-sectional view of a plastic holding device;

FIG. 3 shows a beveled or fish mouth opening in a blood vessel adapted for receiving the device of FIG. 1;

FIG. 4 shows a fragment of the device of FIG. 1 received by a blood vessel;

FIGS. 5 and 6 illustrate suturing methods employing the device of this invention;

FIG. 7 illustrates the device of this invention including a flexible prong;

FIG. 8 illustrates the device of this invention provided with a slidable locking clip with the clip in the open position.

FIG. 9 is a detail drawing of the locking clip;

FIG. 10 shows the mode of assembly of the locking clip onto the blood vessel holding device; and FIG. 11 illustrates the device of this invention provided with a slidable locking clip with the clip in the locked position during use.

FIG. 1 shows a blood vessel holding device 10 which may be metallic and is straight, slender and elongated. In the middle region is an elongated shank 12. On one extremity of shank 12 is a handle region 14 having frictional ridges 16. On the opposite end of shank 12 is a finger or prong 18 which is more slender than either the shank or the handle means. The terminus or extremity 20 of the prong is smooth or rounded. A sharp or pointed hook or wire 22 extends from an intermediate position on the side of prong 18 which may or may not be relatively closer to the shank than the terminus, as desired. The hook projects laterally outwardly from the longitudinal axis of the device and in a direction away from terminus 20 and terminus 20 extends clearly beyond the hook.

FIG. 2 shows in longitudinal cross-sectional view of a device constructed of a flexible plastic material 24 encapsulating a longitudinal wire spine or core 26. The terminus of the spine approximately midway along the finger extends laterally outwardly and rearwardly from the finger to form hook 28. Although shown in straight extension, the plastic shank 30 is flexible and can be bent to provide any desired angle for convenience of use.

FIG. 3 shows an open-ended blood vessel 32 cut in the manner of a slant or bevel to provide a fish mouth opening configuration 34 adapted for receiving the devices of FIGS. 1 and 2.

FIG. 4 illustrates the device of FIG. 1 inserted into the blood vessel of FIG. 3 with terminus 20 of prong 18 entering fish mouth opening 34 to a depth to enable hook 22 to pierce the wall of blood vessel 32 at the distal end of the bevel cut.

FIG. 5 illustrates an end to side technique of anastomosis employing a vein holder of this invention. FIG. 5 shows vein holder 40 ready for removal from the fish mouth opening 42 of vein 44 after disposing the opening 42 in proximate facing relationship with respect to complementary oval shaped opening 46 in the wall of artery 48. The length of the oval opening can extend laterally on the wall of artery 48 instead of longitudinally, as shown, or at any angle therebetween convenient to accommodate the direction of approach to the artery by the open end of the vein. The terminus of the prong is urged against the inside wall of vein 44 near the base of fish mouth opening 42 as indicated at position 43 to prevent collapse of opening 42 during the anastomosis procedure. The holder 40 is used until the sutures 50 taken by means of attached needles 52 can support opening 42 of vein 44 in proximate position with respect to opening 46 of artery 48. For example, such support is accomplished when sutures are completed along one elongated side of oval opening 42, but not the other elongated side of oval opening 42. Thereupon, unhooking and then removal of vein holder 40 from fish mouth opening 42 prevents the device from obstructing completion of the suturing process. After device 40 is removed, the existing sutures are tightened and the partial suturing is completed by taking additional stitches until a continuous blood flow path is provided between vein 44 and artery 48.

FIG. 6 is similar to FIG. 5 except that it illustrates a side to side technique of anastomosis employing a vein holder of this invention. While FIG. 5 shows vein 44 having end opening 42 being sutured, FIG. 6 shows vein 54 having side opening 56 being sutured. Otherwise, the method of anastomosis of FIG. 6 is similar to the method of FIG. 5.

FIG. 7 illustrates a device of this invention having a flexible prong 58 adapted for insertion into a curved blood vessel 60. As shown in FIG. 7, the flexible nature of prong 58 prevents terminus 62 of the prong from obtruding upon the inner wall of blood vessel 60 and injuring said wall.

FIG. 8 shows the blood vessel holding device having slidable locking clip 64 mounted thereon. Locking clip 64 comprises locking clip gripping means 66, locking member 68 and connecting brace 70 connecting gripping means 66 and locking member 68.

FIG. 9 presents a cross-sectional view of locking clip 64 and shows that gripping means 66 is provided with large central opening 72 having protruding key 74 at the top thereof. Locking member 68 has smaller central opening 76 with lateral slot 78 extending from central opening 76 upwardly to connecting brace 70.

FIG. 10 presents an isometric view illustrating the mounting of longitudinally slidable locking clip 64 onto blood vessel holding device 80. FIG. 10 shows that clip 64 can be inserted over prong 82 having rearwardly protruding flexible hook 83. Key 74, shown in FIG. 9, is received by groove 84 on shank 86 to prevent rotation of clip 64 relative to blood vessel holding device 80. When key 74 is received by groove 84 slot 78 is aligned with hook 83 so that locking member 68 can slide past hook 83 until locking member 68 abuts against shoulder 90 of shank 86. This is the retracted position of clip 64 shown in FIG. 8.

Clip 64 and blood vessel holding device 80 can both comprise a plastic material. Clip 64 can be mounted on holding device 80 in a friction tight fit so that clip 64 can only slide on blood vessel holding device 80 upon manual force exerted longitudinally relative to blood vessel holder 80.

FIG. 11 illustrates clip 64 in the locked position during use. As shown in FIG. 11, prong 82 is inserted into the open end of blood vessel 92 and hook 83 penetrates the end of the blood vessel. Then clip 64 is slid downwardly towards the blood vessel until the slotted locking member 68 receives hook 83 to lock the end of blood vessel 92 onto hook 83.

Whereas particular embodiments of the invention have been described for purposes of illustration, it will be evident to those skilled in the art that numerous variations of the details may be made without departing from the invention as defined in the appended claims.

I claim:

1. A blood vessel holding device comprising shank means in a middle region, a handle region on one end of said shank means, and prong means on the other end of said shank means, said prong means having a terminus pointing away from said shank means for inserting into a blood vessel, and sharply pointed hook means extending laterally from an intermediate position on the side of said prong means for hooking through the wall of said blood vessel.

2. The holding device of claim 1 wherein said hook means is a wire.

3. The holding device of claim 1 wherein said hook means is a needle.

4. The holding device of claim 1 wherein said hook means is pointed outwardly and away from said terminus.

5. The holding device of claim 1 which extends straight and rod-like.

6. The holding device of claim 1 wherein said shank means is flexible.

7. The holding device of claim 1 comprising a plastic material encapsulating a wire core.

8. The holding device of claim 7 wherein said hook means is a non-encapsulated extension of said wire core.

9. The holding device of claim 1 wherein said prong means is narrower than said shank means.

10. The holding device of claim 1 including grasping means at said handle region.

11. The holding device of claim 1 wherein said terminus is rounded.

12. A blood vessel holding device comprising shank means in a middle region, a handle region on one end of said shank means, and prong means on the other end of said shank means, said prong means having a terminus pointing away from said shank means for inserting into a blood vessel, and sharply pointed hook means extending from an intermediate position on the side of said prong means in a rearwardly direction for hooking through the wall of said blood vessel.

13. The holding device of claim 1 having longitudinally slidable clip means mounted thereon, said clip means provided with locking means to receive said hook means.

14. The holding device of claim 13 wherein said locking means includes slot means for receiving said hook means.

15. The holding device of claim 13 wherein said slidable clip means is mounted around said holding device.

16. The holding device of claim 13 wherein said slidable clip means comprises slidable clip gripping means mounted around said shank means, said locking means mounted around said prong means and brace means connecting said slidable clip gripping means to said locking means.

17. A blood vessel holding device comprising shank means in a middle region, a handle region on one end of said shank means, prong means on the other end of said shank means, said prong means having a terminus pointing away from said shank means for inserting into a blood vessel, sharply pointed hook means extending from an intermediate position on the side of said prong means in a rearwardly direction for hooking through the wall of said blood vessel, and locking means mounted on said holding device for locking said blood vessel onto said hook means.

18. The holding device of claim 17 wherein said locking means is longitudinally slidable on said holding device.

19. The holding device of claim 17 wherein said locking means is mounted in friction tight association around said holding device.

20. The holding device of claim 17 wherein said locking means includes slot means for receiving said hook means.

21. The holding device of claim 1 wherein said prong means is flexible.

22. The holding device of claim 12 wherein said prong means is flexible.

23. A method for suturing the open end of a first blood vessel to an opening in a second blood vessel to form a continuous channel for blood flow between said blood vessels comprising inserting a prong having a forward terminus end for insertion into the blood vessel and a sharply pointed hook means extending from an intermediate position on the side thereof into the open end of said first blood vessel, piercing said hook means through the wall of said first blood vessel to secure said first blood vessel, disposing said prong so that said open end of said first blood vessel is in proximate facing relationship with respect to said opening in said second blood vessel, partially suturing said first blood vessel to said second blood vessel to incompletely secure said blood vessels to each other, detaching said hook means, withdrawing said prong from said first blood vessel and completing said suturing method.

24. The method of claim 23 performed during coronary bypass surgery.

25. The method of claim 23 wherein said open end of said first blood vessel is beveled to provide a fish mouth opening shape.

26. The method of claim 23 wherein said opening in said second blood vessel is in the wall of said second blood vessel.

27. The method of claim 23 wherein said first blood vessel is a vein and said second blood vessel is an artery.

28. The method of claim 23 wherein in said inserting step said prong is urged against the inside wall of said first blood vessel opposite from the point of piercing with said hook means to prevent collapse of the open end of said first blood vessel.

29. The method of claim 23 wherein said prong is flexed as it is inserted into said first blood vessel to conform with the shape of said first blood vessel.

30. The method of claim 23 including the step of locking said first blood vessel onto said hook means.

* * * * *